(12) United States Patent
Santini, Jr. et al.

(10) Patent No.: US 7,070,592 B2
(45) Date of Patent: Jul. 4, 2006

(54) MEDICAL DEVICE WITH ARRAY OF ELECTRODE-CONTAINING RESERVOIRS

(75) Inventors: John T. Santini, Jr., Belmont, MA (US); Michael J. Cima, Winchester, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 7 days.

(21) Appl. No.: 10/886,405

(22) Filed: Jul. 7, 2004

(65) Prior Publication Data

US 2004/0248320 A1 Dec. 9, 2004

Related U.S. Application Data

(62) Division of application No. 09/727,858, filed on Dec. 1, 2000, now Pat. No. 6,808,522.

(60) Provisional application No. 60/170,218, filed on Dec. 10, 1999.

(51) Int. Cl.
*A61K 9/22* (2006.01)
*A61N 1/30* (2006.01)

(52) U.S. Cl. ...................... 604/891.1; 604/20

(58) Field of Classification Search ............. 604/890.1, 604/891.1, 20, 501, 87–90, 93.01, 99.04; 128/898; 600/300; 607/3
See application file for complete search history.

(56) References Cited

U.S. PATENT DOCUMENTS

| | | | |
|---|---|---|---|
| 3,692,027 A | 9/1972 | Ellinwood, Jr. | |
| 4,360,019 A | 11/1982 | Portner et al. | |
| 4,507,115 A | 3/1985 | Kambara et al. | |
| 4,585,652 A | 4/1986 | Miller et al. | |
| 4,731,049 A | 3/1988 | Parsi | |
| 4,731,051 A | 3/1988 | Fischell | |
| 4,793,825 A | 12/1988 | Benjamin et al. | |
| 4,874,500 A * | 10/1989 | Madou et al. | ............. 204/412 |
| 5,041,107 A | 8/1991 | Heil, Jr. | |
| 5,042,975 A | 8/1991 | Chien et al. | |
| 5,147,297 A | 9/1992 | Myers et al. | |

(Continued)

FOREIGN PATENT DOCUMENTS

DE 296 998 A5 7/1988

(Continued)

OTHER PUBLICATIONS

Bae, et al., "*Pulsatile Drug Release by Electric Stimulus,*" ACS Symp. Series Polymeric Drugs & Drug Admin., pp. 99-110 (1994).

(Continued)

*Primary Examiner*—Sharon Kennedy
(74) *Attorney, Agent, or Firm*—Sutherland Asbill & Brennan LLP

(57) ABSTRACT

Devices are provided for medical diagnostics comprising a substrate; an array of reservoirs; one or more electrodes located at least partially inside the reservoirs; a plurality of discrete reservoir caps covering openings in the plurality reservoirs; control circuitry for selectively disintegrating or permeabilizing the reservoir cap over a reservoir opening; and, optionally, a diagnostic reagent in the reservoirs. Devices also are provided for the controlled delivery of molecules comprising a substrate; an array of reservoirs; a release system in the reservoirs comprising molecules for release; one or more electrodes attached to the substrate inside the reservoirs or to a surface outside of the reservoirs, wherein the electrodes are not reservoir caps; and means for applying an electric current or potential across the electrodes effective to activate release of the molecules from the reservoirs. The devices can be adapted for implantation for in vivo diagnostics or drug delivery.

29 Claims, 10 Drawing Sheets

U.S. PATENT DOCUMENTS

| | | | |
|---|---|---|---|
| 5,167,625 | A | 12/1992 | Jacobsen et al. |
| 5,170,801 | A | 12/1992 | Casper et al. |
| 5,200,051 | A | 4/1993 | Cozzette et al. |
| 5,252,294 | A | 10/1993 | Kroy et al. |
| 5,254,081 | A | 10/1993 | Maurer et al. |
| 5,279,607 | A | 1/1994 | Schentag et al. |
| 5,318,557 | A | 6/1994 | Gross |
| 5,324,316 | A | 6/1994 | Schulman et al. |
| 5,366,454 | A | 11/1994 | Currie et al. |
| 5,368,588 | A | 11/1994 | Bettinger |
| 5,368,704 | A | 11/1994 | Madou et al. |
| 5,443,508 | A | 8/1995 | Giampapa |
| 5,474,527 | A | 12/1995 | Bettinger |
| 5,533,995 | A | 7/1996 | Corish et al. |
| 5,585,069 | A | 12/1996 | Zanzucchi et al. |
| 5,605,662 | A | 2/1997 | Heller et al. |
| 5,770,076 | A | 6/1998 | Chu et al. |
| 5,782,799 | A | 7/1998 | Jacobsen et al. |
| 5,797,898 | A | 8/1998 | Santini, Jr. et al. |
| 5,893,974 | A | 4/1999 | Keller et al. |
| 5,900,160 | A | 5/1999 | Whitesides et al. |
| 5,962,081 | A | 10/1999 | Ohman et al. |
| 5,985,328 | A | 11/1999 | Chu et al. |
| 5,989,445 | A | 11/1999 | Wise et al. |
| 6,056,734 | A | 5/2000 | Jacobsen et al. |
| 6,066,163 | A | 5/2000 | John |
| 6,114,658 | A | 9/2000 | Roth et al. |
| 6,123,861 | A | 9/2000 | Santini, Jr. et al. |
| 6,163,720 | A | 12/2000 | Gyory et al. |
| 6,232,150 | B1 | 5/2001 | Lin et al. |
| 6,248,540 | B1 | 6/2001 | Weinberg et al. |
| 6,251,688 | B1 | 6/2001 | Erb et al. |
| 6,261,584 | B1 | 7/2001 | Peery et al. |
| 6,288,888 | B1 | 9/2001 | Sakata et al. |
| 6,306,420 | B1 | 10/2001 | Cheikh |
| 6,331,439 | B1 | 12/2001 | Cherukuri et al. |
| 6,334,859 | B1 | 1/2002 | Richter |
| 6,491,666 | B1 | 12/2002 | Santini, Jr. et al. |
| 6,527,762 | B1 | 3/2003 | Santini, Jr. et al. |
| 6,537,256 | B1 | 3/2003 | Santini, Jr. et al. |
| 6,551,838 | B1 | 4/2003 | Santini, Jr. et al. |
| 6,571,125 | B1 | 5/2003 | Thompson |
| 6,656,162 | B1 | 12/2003 | Santini, Jr. et al. |
| 6,663,615 | B1 | 12/2003 | Madou et al. |
| 6,669,683 | B1 | 12/2003 | Santini, Jr. et al. |
| 6,709,379 | B1 | 3/2004 | Brandau et al. |
| 6,730,072 | B1 | 5/2004 | Shawgo et al. |
| 6,773,429 | B1 | 8/2004 | Sheppard, Jr. et al. |
| 6,827,250 | B1 | 12/2004 | Uhland et al. |
| 2002/0022826 | A1 | 2/2002 | Reynolds et al. |
| 2002/0072784 | A1 | 6/2002 | Sheppard, Jr., et al. |
| 2002/0099359 | A1 | 7/2002 | Santini, Jr., et al. |
| 2002/0111658 | A1 | 8/2002 | Greenberg et al. |
| 2002/0183721 | A1 | 12/2002 | Santini, Jr. et al. |
| 2002/0187260 | A1 | 12/2002 | Sheppard, Jr., et al. |
| 2002/0188282 | A1 | 12/2002 | Greenberg |
| 2003/0032946 | A1 | 2/2003 | Fishman |
| 2003/0055344 | A1 | 3/2003 | Eigler et al. |
| 2003/0055345 | A1 | 3/2003 | Eigler et al. |
| 2003/0069560 | A1 | 4/2003 | Adamis et al. |
| 2003/0104590 | A1 | 6/2003 | Santini, Jr., et al. |
| 2003/0105455 | A1 | 6/2003 | Santini, Jr. et al. |
| 2004/0106953 | A1 | 6/2004 | Yomtov et al. |

FOREIGN PATENT DOCUMENTS

| | | |
|---|---|---|
| DE | 39 08 822 A1 | 3/1989 |
| DE | 197 16 683 C1 | 6/1998 |
| WO | WO 93/03790 A1 | 3/1993 |
| WO | WO 98/46325 A1 | 10/1998 |
| WO | WO 99/03684 A1 | 1/1999 |
| WO | WO 02/056862 A1 | 7/2002 |
| WO | WO 02/058678 A2 | 8/2002 |

OTHER PUBLICATIONS

Becker, et al., "*Hot Embossing as a Method for the Fabrication of Polymer High Aspect Ratio Structures,*" Sensors and Actuators. 83:130-135 (2000).

Becker, et al., "*Polymer microfabrication methods for microfluidic analytical methods,*" Electrophoresis 21:12-26 (2000).

Becker, et al., "*Planar quartz chips with submicron channels for two-dimensional capillary electrophoresis applications,*" J. Micromech Microeng. 8:24-28 (1998).

Frankenthal, et al., *J. Electrochem. Soc.*, May 1976.

Izumi, et al., *J. Electroanal. Chem.* 303: 151-60 (1991).

Jackman, et al., "*Fabricating Large Arrays of Microwells with Arbitrary Dimensional and Filling Them Using Discontinuous Dewetting,*" Anal. Chem. 70:2280-2287 (1998).

Kano, et al., *Analytical Sciences* 16: 1013-21 (2000).

Kwon, et al., "*Electrically Erodible Polymer Gel For Controlled Release of Drugs,*" Nature 354: 291-93 (1991).

Low, et al., "*Microactuators Towards Microvalves for Responsive Controlled Drug Delivery,*" Sensors & Actuators B. 67:149-60 (2000).

Madou, et al., "*Exploitation of a Novel Artificial Muscle for Controlled Drug Delivery,*" pp. 495-497 (1999).

McCormick, et al., "*Microchannel Electrophoretic Separations of DNA in Injection-Molded Plastic Substrates,*" Analytical Chemistry. 69:2626-2630 (1997).

Sassi, et al., "*Electrophoresis of DNA in novel thermoreversible matrices,*" Electrophoresis. 17: 1460-69 (1996).

Schaefer, *Novartis Found. Symp.* 2000; 227:225-39 (abstract).

Schwarz, et al., pp. 461-65, *1st Ann. Intl. IEEE-EMBS Spec. Topic. Conf. Microtech. Medicine & Biology* (Lyon, France, Oct. 2000).

Surbled, et al., "*Characterization of Sputtered TiNi Shape Memory Alloy Thin Films,*" Japanese Journal of Applied Physics. 38: L1547-L1549 (1999).

Surbled, et al., "*Shape Memory Alloys for Micromembranes Actuation,*" SPIE. 3825:63-70 (1999).

Surbled, et al., "*Array of Shape Memory Alloy One-Shot Micro-Valves for Drug Delivery,*" MME '99, Gif sur Yvette, France (Sep. 27-28, 1999).

Tierney, et al., "*New Electrorelease Systems Based on Microporous Membranes,*" J. Electrochem. Soc., 137:3789-3793 (1990).

Tierney, et al., "*Electroreleasing Composite Membranes for Delivery of Insulin and Other Biomacromolecules,*" J. Electrochem. Soc., 137:2005-2006 (1990).

\* cited by examiner

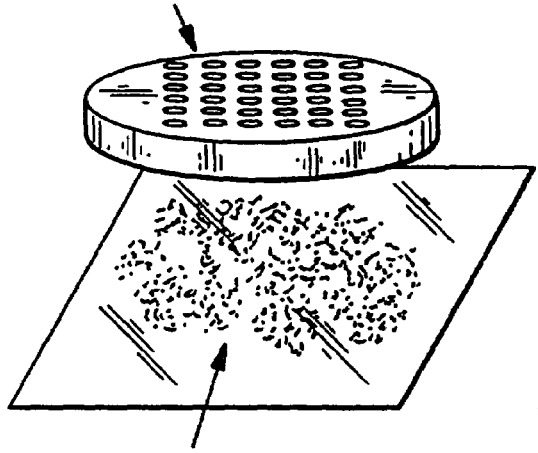
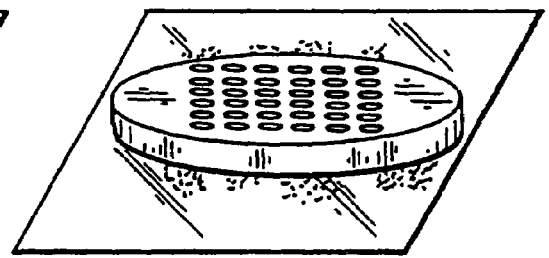
FIG. 9A
FIG. 9B
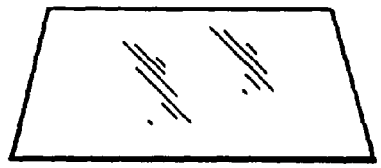
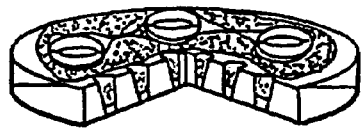
FIG. 9C
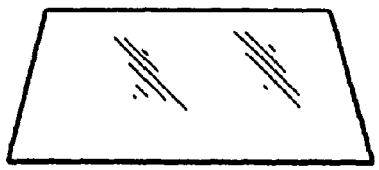
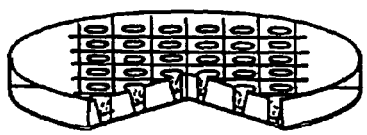
FIG. 9D METHOD FOR SEALING MICROCHIP DEVICE USING ULTRASONIC WELDING. WELDING COULD BE PERFORMED ALONG THE INDICATED LINES.

METHOD FOR SEALING MICROCHIP DEVICE USING FRAME, GASKET, AND BOLTS OR OTHER FASTENERS.

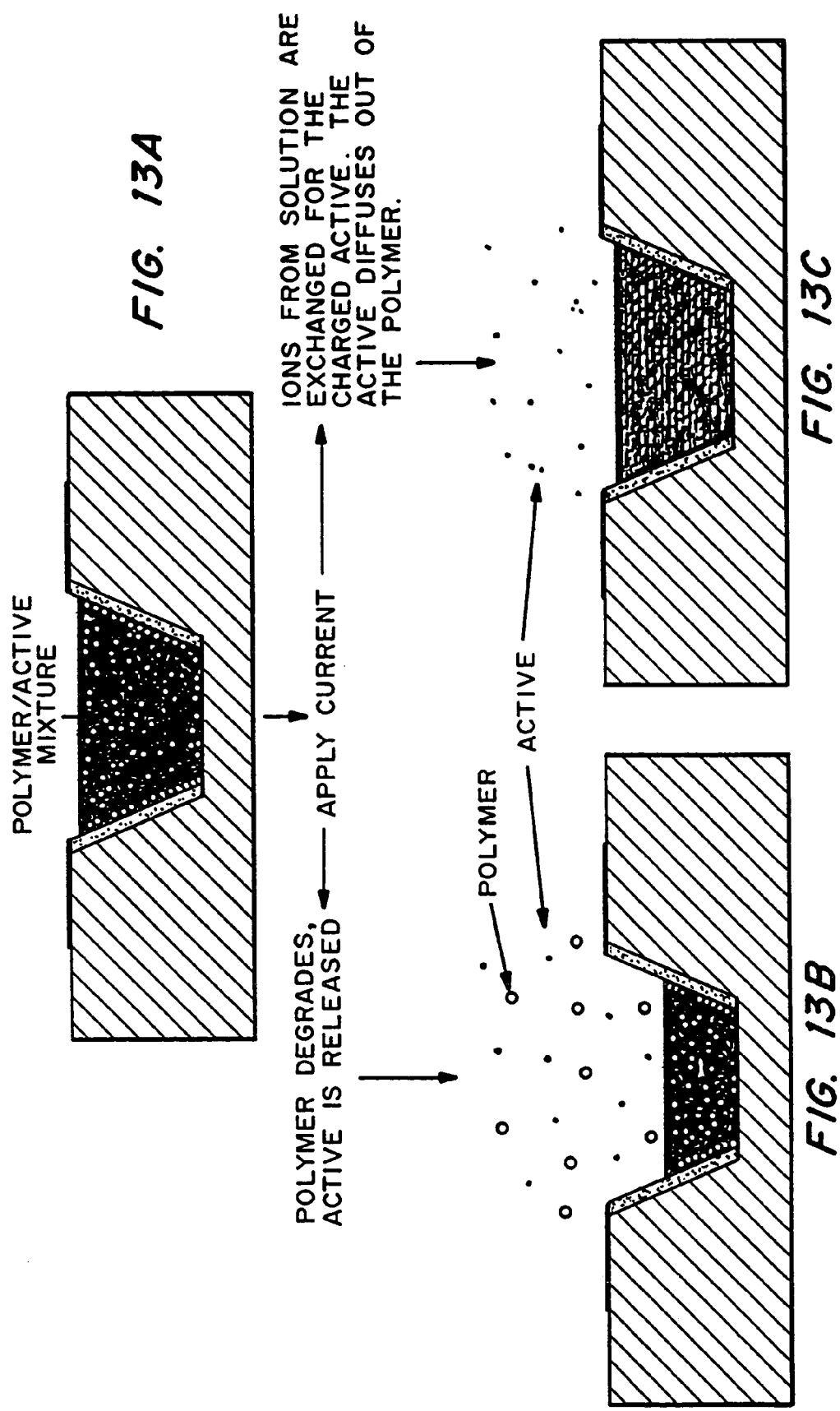

MEDICAL DEVICE WITH ARRAY OF ELECTRODE-CONTAINING RESERVOIRS

CROSS-REFERENCE TO RELATED APPLICATIONS

This is a divisional of U.S. application Ser. No. 09/727,858, filed Dec. 1, 2000, now U.S. Pat. No. 6,808,522. Application Ser. No. 09/727,858 claims benefit of U.S. Provisional Application No. 60/170,218, filed Dec. 10, 1999. All of these applications are incorporated herein by reference in their entirety.

STATEMENT REGARDING FEDERALLY SPONSORED RESEARCH OR DEVELOPMENT

This invention was made with government support under NIH—R24-AI47739 awarded by the National Institutes of Health. The government has certain rights in the invention.

BACKGROUND OF THE INVENTION

This invention relates to miniaturized drug delivery devices and more particularly, to controlled time and rate release multi-welled drug delivery devices.

The efficacy of many drugs is directly related to the way in which they are administered. A wide variety of methods for controlled release have been developed, including pumps, patches, tablets, and implants. However, all of these methods have unique disadvantages when considering the treatment of a chronic condition. A major disadvantage of both external and internal micropumps is that they depend on the reliable operation of moving parts. Failure of the pump due to breakage, leakage, or clogging may be catastrophic for the individual. Patches are useful only for certain chemicals that may be absorbed through the skin. Tablets are widely used but can achieve release for only a limited amount of time before they pass through the digestive system. Many polymeric materials proposed to be used for pulsatile release of a chemical are responsive to changes in pH or temperature (Lee, et al., *J. Appl. Polym. Sci.*, 62:301–11 (1996)), the application of ultrasound (Kost, et al., *Proc. Nat. Acad. Sci., USA*, 86:7663–66 (1989); Levy, et al., *J. Clin. Invest.*, 83:2074–78 (1989)), changes in enzymes, or changes in electric (Kwon, et al., *Nature*, 354:291–93 (1991)) or magnetic (Kost, et al., *J. Biomed. Mater. Res.*, 21:1367–73 (1987)) fields. These polymeric systems are limited to the release of only one or a few chemicals, and may need to be tailored to the specific condition which they are to treat (glucose-sensitive insulin release systems for the treatment of diabetes, for example (Kitano, et al., *J. Control. Release*, 19:162–70 (1992))). Additionally, the stimuli source may be large, expensive, or too complex for frequent use. Moreover, fabrication procedures for implants such as microspheres are usually complex, and the solvents or heat used during fabrication can adversely affect the stability of the drugs contained in the microspheres.

U.S. Pat. No. 5,797,898 and U.S. Pat. No. 6,123,861, to Santini, et al., describe active and passive microchips for drug delivery. However, the fabrication methods described therein are primarily based on standard microelectronics processing techniques. It would be advantageous to provide additional, preferably simple and inexpensive, methods of manufacturing such microchip devices. It would also be advantageous to develop new methods of triggering and controlling release of the molecules.

PCT WO 99/03684 discloses a process of making a device having a surface microstructure of wells or channels using a low cost process of screen printing a curable or polymerizable material onto a plastic substrate and then curing or polymerizing the material. The device can contain hundreds of wells and be used as a microtitre plate array, holding reagents of interest, but it is not designed to provide any sort of controlled release or delivery function.

It is therefore an object of the present invention to provide a variety of techniques for the manufacture, particularly the low cost manufacture, of multi-welled microchip devices for the controlled release of drugs and other molecules.

It is another object of the present invention to provide a device that allows delivery of drugs or other molecules in either a pulsatile or continuous manner, using a variety of materials of construction and methods for triggering and controlling release of the molecules.

SUMMARY OF THE INVENTION

Methods are provided for manufacturing microchip devices for the storage and controlled release of molecules, such as drugs. Methods include compression molding, injection molding, thermoforming, casting, and combinations of these techniques, alone or in combination with microfabrication techniques. The methods are adapted to make either active or passive release devices from materials such as polymers, ceramics, and metals. In a preferred embodiment, polymeric devices are made by (1) filling a die with a polymer powder; (2) compressing the powder to form a partially or completely dense polymer preform; (3) thermal compression molding the preform in a mold to form a substrate, wherein the mold has a plurality of protrusions which form reservoirs in the substrate; and (4) filling the reservoirs with a release system comprising the molecules to be released. Alternatively, ceramic devices are formed from a ceramic powder or a slurry thereof which is cast in a mold to form the substrate, again wherein the mold has a plurality of protrusions which form reservoirs in the substrate.

Each filled reservoir optionally can include reservoir caps that control release. In devices of any substrate material, methods of forming reservoir caps can utilize capillary action depending upon the selection of appropriate reservoir dimensions.

These fabrication methods preferably further include exposing (i.e. opening) the ends of the reservoirs after molding or casting, by cutting the substrate, planarizing the surface of the substrate, or a combination of these techniques.

The release system may be formed solely of the molecules to be released in pure form or the molecules may be combined with a release-controlling component, such as a polymeric matrix, which affects the release rate and time through degradation, dissolution, swelling, or disintegration of the component. The release system also may include a material that does not undergo such processes, but affects the molecule release rate via diffusion of the molecules through the material. In one embodiment of active release systems, the reservoirs are provided with a cap that covers the reservoir and responds directly to an applied external stimulus (e.g., an applied voltage or potential), or to a change in the local environment of the device or reservoir, which is brought about by the application of the external stimulus (e.g., local pH change or generation of an electric field due to the application of a voltage or potential to electrodes in or near the reservoir). In a preferred embodiment, active release devices are provided with electrodes positioned in, near, or partially covering the reservoirs, such that upon application of an electric potential or current across the electrodes, the release system (1) degrades due to local pH changes or (2) exchanges ions in solution with an ionically bound active substance, thereby releasing the molecules from the release system. For example, the release system can be a biodegradable matrix. In another embodiment, the electrodes drive charged molecules from the release system upon application of an electric current across the electrodes.

BRIEF DESCRIPTION OF THE FIGURES

FIGS. 9a–f illustrate several embodiments of methods for sealing the reservoirs of the device.

FIGS. 13a–c are cross-sectional side views of one embodiment of an active device having electrodes on side walls of a reservoir containing polymer/active agent matrix (13a) for a polymer that degrades upon application of an electrical current through the electrodes (13b) and for a polymer that undergoes ion exchange upon application of the electrical current (13c).

DETAILED DESCRIPTION OF THE INVENTION

Figure 1:
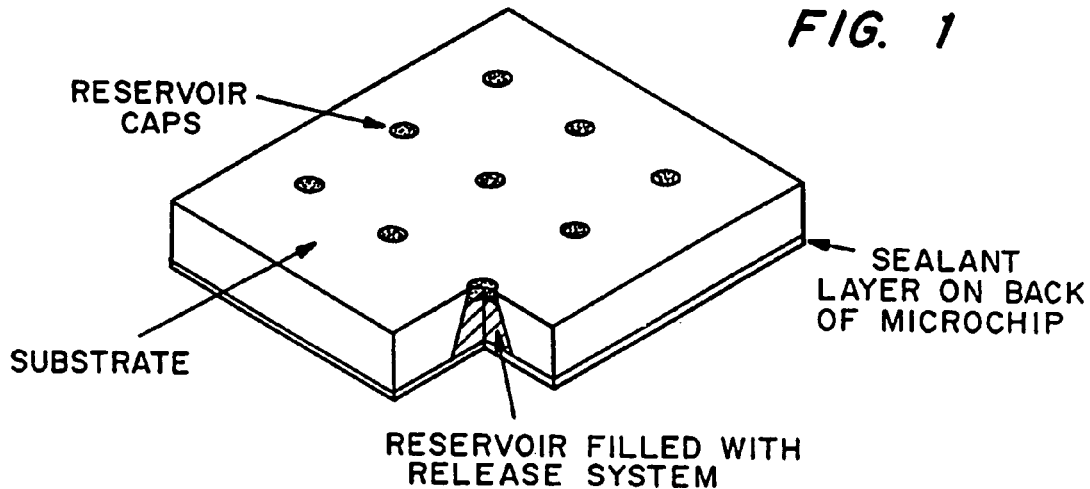
FIG. 1 is a schematic illustrating one embodiment of a passive delivery device having reservoir caps and reservoirs filled with a release system.

Microchip devices are provided which can accurately deliver precise quantities of molecules at defined rates and times according to the needs of the patient or experimental system. As used herein, a "microchip" is defined as a miniaturized device fabricated using forming methods such as compression molding, injection molding, thermoforming, or other methods described in, for example, Tadmor & Gogos, *Principles of Polymer Processing*, (John Wiley & Sons, New York 1979), microinjection, microcontact printing, standard microelectronics processing methods such as photolithography, etching, evaporation, and sputtering as described, for example, in Wolf & Tauber, *Silicon Processing for the VLSI Era, Volume I-Process Technology* (Lattice Press, Sunset Beach, Cal. 1986); Jaeger, *Introduction to Microelectronic Fabrication, Volume V* in *The Modular Series on Solid State Devices* (Addison-Wesley, Reading, Mass. 1988); and Campbell, *The Science and Engineering of Microelectronic Fabrication* (Oxford University Press, New York 1996); microfabrication methods described, for example, in Madou, *Fundamentals of Microfabrication* (CRC Press, 1997); and combinations of these methods. The microchips provide control over the rate at which the molecules are released, as well as the time at which release starts.

The fabrication methods described herein may be used to fabricate devices having primary dimensions (length of a side for square or rectangular devices, or diameter for round devices) that are typically a few centimeters, and preferably a few millimeters, or smaller. Device dimensions may vary depending on the application. The number and volume of the reservoirs varies with the device dimensions. Devices for in vivo applications are small enough to be implanted, injected, orally administered, or attached to various mucous membranes.

Release of molecules can be controlled actively, passively, or by a combination thereof. Passive devices do not require the application of a stimuli source to effect these changes. Representative methods of release (i.e. triggering mechanisms) for passive devices include disintegration of a reservoir cap, or diffusion from a release system containing the pure molecules to be released or a mixture of the molecules and an excipient material that affects the release rate and/or time.

As used herein, unless explicitly indicated otherwise, the terms "disintegrate" or "disintegration" in reference to reservoir caps or release system matrix refer to the loss of structural integrity by any mechanism, including, but not limited to, physical fracture, rupture, or deformation, chemical or enzymatic degradation, and dissolution. This includes rupture of the reservoir cap resulting from swelling of the reservoir cap, the release system, or both.

As used herein, the term "release system" includes the molecules in their pure form (solid, liquid, or gel), as well as the molecules in combination with other materials that affect the rate and/or time of release of the molecules. These other materials can be, for example, a matrix formed of a biodegradable material or a material that releases the incorporated molecules by diffusion or disintegration of the matrix. The "release system" includes mixtures of different forms (e.g., solid, liquid, and/or gel) of the molecules, as well as mixtures of the molecules with various excipient or release-controlling materials that disintegrate. A release system also may include a material that does not undergo any of the above processes, but affects the release rate of the molecules as they diffuse through it.

Active devices may be controlled by microprocessors, remote control, or biosensors. Typical control methods include electric potential and pH control methods. In one embodiment, the application of an electric current or potential causes electrochemical reactions to occur which trigger disintegration or another change in the reservoir cap or release system, which can affect both release rate and time. Alternatively, an applied electric potential or current can change the pH in the local environment around a reservoir cap or release system, causing a change in the reservoir cap or release system materials, which can also affect the release rate and/or time. Examples of release methods include simple dissolution of a reservoir cap due to an electrochemical reaction, electrophoretic delivery of molecules from a release system in a reservoir, release of molecules from a reservoir due to ion exchange, or swelling of a release system which causes the reservoir cap to rupture, thereby releasing the molecules from the reservoir.

I. Device Components and Materials

The microchip devices can be described as "passive devices" or "active devices." Both types control the rate and time of release of the molecules.

Each microchip device, whether passive or active, includes a substrate, a plurality of reservoirs, and a release system, similar to that described in U.S. Pat. No. 5,797,898 and U.S. Pat. No. 6,123,861, to Santini, et al. The reservoirs optionally include reservoir caps, electrodes, or both.

Substrate

The substrate of the passive and active microchip devices can be composed of any suitable material that can be fabricated by the methods described herein. Representative materials include polymers, such as poly(ethylene), poly (tetrafluoroethylene) and other fluorinated polymers, silicones (poly(siloxanes)), and copolymers thereof. Preferred biodegradable polymers include, for example, poly(anhydrides), polyphosphazenes, pseudo poly(amino acids), and poly(esters) such as poly(lactide), poly(glycolide), and poly (lactone)s, and copolymers thereof. Other representative materials of construction include metals; semi-conductors, such as silicon; and ceramic materials, such as alumina (aluminum oxide), aluminum nitride, silicon dioxide, silicon nitride, and other various nitrides and oxides.

For in vivo applications, the substrate can be formed or coated with a biocompatible material. For in vitro applications, such as in the field of medical diagnostics, the substrate can be constructed of biocompatible or non-biocompatible materials.

Reservoir Caps and Release Systems

Figure 2:
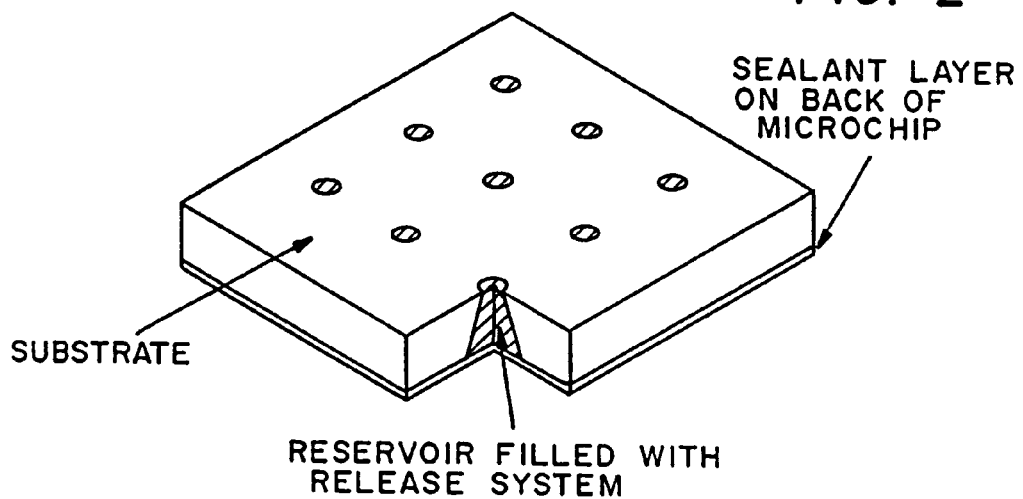
FIG. 2 is a schematic illustrating one embodiment of a passive delivery device having no reservoir caps and reservoirs filled with a release system.

The reservoirs optionally include reservoir caps. Reservoir caps control the release time (and in some cases, release rate) of the molecules by disintegrating or by affecting diffusion of the molecules through the reservoir cap material. Combinations of both the reservoir caps and release systems may be used to achieve the desired release time and rate for the molecules. FIG. 1 and FIG. 2 illustrate examples of passive release devices with reservoir caps (FIG. 1) and without reservoir caps (FIG. 2).

Figure 3:
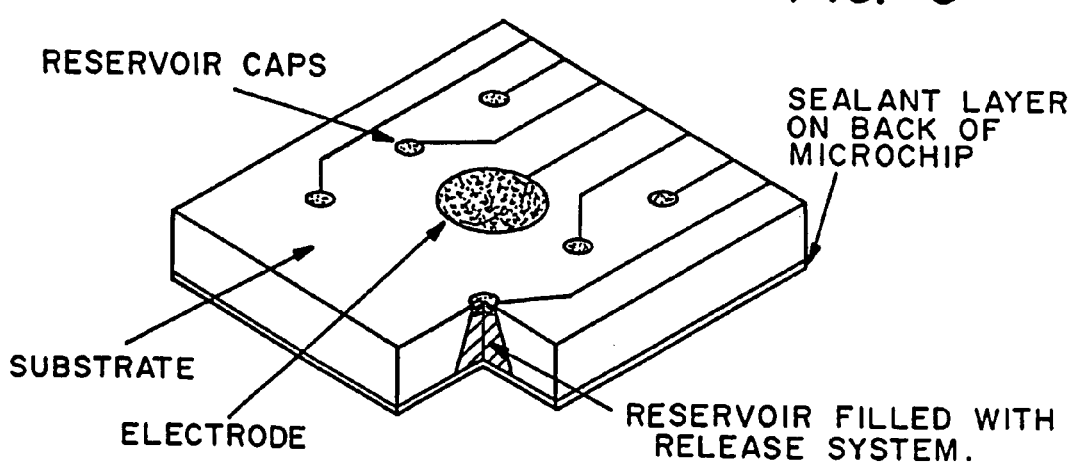
FIG. 3 is a schematic illustrating one embodiment of an active delivery device having electrically responsive reservoir caps and reservoirs filled with a release system.

An additional release mechanism for active devices comprises a reservoir cap that covers the reservoir of interest and is responsive to a directly applied stimulus or stimuli (e.g., an applied voltage or potential), or to a change in the local environment of the device or reservoir, which is brought about by the application of a stimulus (e.g., local pH change or generation of an electric field due to the application of a voltage or potential to electrodes in or near the reservoir). Other representative examples of stimuli that can be applied to induce the response include heat, light (e.g., laser), and magnetic field. FIG. 3 illustrates an embodiment of an active microchip device having reservoirs covered by electrically responsive caps. Other release mechanisms for active devices include combinations of these stimuli responsive caps (i.e. active caps) with one or more additional reservoir caps, either active or passive, located underneath the stimuli responsive cap (e.g., inside the reservoir), which disintegrate after the active cap is removed or made permeable.

For embodiments of these devices (both passive and active) in which it is desired to release molecules over a short period of time, reservoir caps or release systems, such as matrices, may be fabricated from quickly disintegrating materials including, for example, poly(lactide-co-glycolide) copolymers containing a high glycolide content, copolymers of poly(lactones) with fast degradation times, certain poly (anhydrides), hydrogels, oligosaccharides, polysaccharides, and rolled metal foils or evaporated, sputtered, or chemical vapor deposited (CVD) thin films (copper films, for example). For applications in which a longer use time is desirable, reservoir caps and release systems can be fabricated from materials that take longer to disintegrate. Examples include resorbable biological materials such as cholesterol, other lipids and fats, and lipid bilayers, polymers such as poly(caprolactone) or certain poly(anhydrides), and PLGA copolymers with high lactic acid content. For structures in which the molecules to be released must diffuse through a release system matrix, reservoir cap and/or release system materials may remain intact or disintegrate.

For an active device, reservoir caps can be fabricated from non-conducting materials such as the polymers described above or conducting polymers including, for example, polyaniline or polypyrrole. Electrically erodible polymers such as complexes of poly(ethyloxazoline) and poly(methacrylic acid) can be used as a component of a release system (Kwon, et al., *Nature*, 354:291–93 (1991)), or a reservoir cap. Conducting polymers such as polypyrrole can be mixed with a chemical and used to deliver the chemical via electrophoresis (Miller, *Mol. Cryst. Liq. Cryst.*, 160:297–301 (1988)). Electrodes, circuitry, and conducting reservoir caps which cover the reservoirs can be fabricated from materials including, for example, conducting polymers such as polyaniline or polypyrrole, and metals such as copper, gold, platinum, and silver. Non-conducting, responsive reservoir caps can be made from materials such as polymers that are sensitive to pH, electric field, or other environmental conditions.

In some embodiments, the release system responds to the application of an electric current by either degrading or exchanging ions from solution with an active agent that is ionically bound to the polymer. Examples of materials for such release systems include copolymers of poly(ethyloxazoline) and poly(methacrylic acid), which have been shown to degrade with an applied current. Other examples include release of edrophonium chloride (a positively charged molecule) through an ion-exchange mechanism using a copolymer of 2-acrylamido-2-methyl-1-propane sulfonic acid and n-butylmethacrylate, or release of dopamine from a composite polymer of poly(N-methylpyrrole)-poly(styrene sulfonate), upon application of an applied current.

Electrodes

In preferred embodiments, the microchip device includes one or more electrodes that do not seal reservoirs (as a reservoir cap would). Rather, the electrodes are located inside a reservoir; on a surface outside of a reservoir but near enough to the reservoir to effect a change in its release system (or reservoir cap if present) when the electrodes are activated (i.e. electric current or potential applied across the electrodes); partially covering the reservoir (and reservoir cap if present); or a combination thereof.

The electrodes typically are thin films of a conducting metal or doped semiconductor.

Molecules to be Released

A wide variety of molecules can be contained in and released from the microchip devices. Examples of the molecules include drugs, diagnostic reagents, fragrances, dyes or coloring agents, sweeteners and other flavoring agents, and compounds used in tissue culture, such as cellular growth factors.

The molecules to be released from the microchip device may be in solid, liquid, or gel form, and may be in pure form or mixed with other materials that affect the release rate and/or time, by forming a phase or by providing a diffusional barrier, for example. Molecules can be in the form of solid mixtures such as amorphous and crystalline mixed powders, monolithic solid mixtures, and solid interpenetrating networks; in the form of liquid mixtures including, for example, solutions, emulsions, colloidal suspensions, and slurries; and in the form of gel mixtures such as hydrogels.

For in vivo applications, the molecules preferably are a therapeutic, prophylactic, or diagnostic agent. Examples include chemotherapeutic agents, hormones, and painkillers. It is particularly advantageous to deliver bioactive molecules that are efficacious in very small quantities, such as hormones and steroids.

The quantity of material that can be placed in a microchip is highly dependent on the volume of the microchip device and its geometry. Typical volumes for each square pyramid-shaped reservoir in a substrate can range from a few nanoliters (nl or nL) to a few microliters (µl or µL). Accordingly, larger devices (e.g., 6 cm×6 cm×2.5 cm) can store and release several grams of material (e.g., drug), while smaller devices (2 mm by 2 mm by 0.3 mm) can store and release as little material as desired (e.g., sub-nanogram quantities). Similar calculations can be utilized for any substrate material, device geometry, reservoir shape and size, and molecules to be delivered. For example, a square pyramid reservoir having one 50 µm by 50 µm opening and one 500 µm by 500 µm opening in a 300 µm thick substrate would have a volume of approximately 26 nl. If a density of 1 g/cm$^3$ is assumed for the release system placed into the reservoir, then this reservoir will hold approximately 26 µg of release system.

In one embodiment having a polymer substrate, the substrate is circular, about 0.5 inches (1.3 cm) in diameter. The thickness can vary (e.g., depending on the extent of polishing), and the volume of each reservoir typically varies with the substrate thickness. In this embodiment, the reservoirs are each conical in shape with an interior angle of about 70°. The base of the cone is about 728 µm in diameter, and the height of the cone is about 1000 µm. This embodiment has 36 reservoirs, spaced about 500 µm apart (i.e. about 500 µm between the bases of the conical openings), in a 6×6 square array (about 6.8 mm×6.8 mm). For a reservoir opening (small end of cone) of 300 µm in diameter, the substrate is 588 µm thick and the reservoir volume is 129 nL. For a reservoir opening of 50 µm in diameter, the substrate is 931 µm thick and the reservoir volume is 138 nL. It is apparent that one can readily change the number, arrangement, and geometry (size and shape) of the reservoirs as needed, for example to suit a particular application or based on manufacturing considerations.

II. Methods of Fabricating the Devices

The microchip devices can be made using the methods described below, alone or in combination with the methods described in U.S. Pat. No. 5,797,898 and U.S. Pat. No. 6,123,861, to Santini, et al., which are hereby incorporated by reference.

Fabrication of the Substrate and Reservoirs

In a preferred fabrication method, polymer powder is compression molded at low temperature (below the $T_g$ of the polymer) into a partially dense preform (see FIG. 4). The preform is subsequently compression molded at a temperature between the $T_g$ of the polymer ±10° C. and its degradation temperature. This compression step involves molding of the preform on an indenter plate, fabricated out of a metal, ceramic, or other suitable rigid material, in order to create reservoirs in the substrate (see FIG. 5). An intermediate compression molding step may be included to density the preform before it is molded on the indenter plate. Alternatively, the preform may be directly molded on the indenter plate, combining the indentation and densification steps. Complete densification of the substrate is desirable for most applications, but residual porosity may be useful for certain applications in which diffusion of molecules into or out of the device is desirable.

Other forming methods, such as injection molding, thermoforming, casting, and other methods known to those skilled in the art can be used to form a substrate out of a polymer, other materials (e.g., metals), or combinations thereof.

In another useful fabrication method, a ceramic powder is cast in a mold that has indenters, whereby a preliminary reservoir-containing substrate is formed via drying of the slurry in the mold. The preliminary substrate (green part) is then fired to density the part.

Figure 6A:
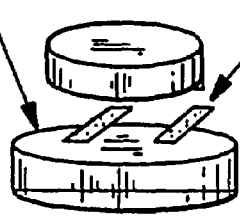
FIGS. 6a–c illustrate one embodiment of a polishing step for exposing the reservoir ends of a substrate having reservoirs formed on one side.

Reservoirs as initially fabricated may or may not completely penetrate the substrate, depending on the type of indenter plate used for compression molding, or the configuration of molds used for other forming methods. For fabrication methods in which the reservoirs as fabricated do not initially penetrate completely through the substrate, the reservoir ends may be exposed by one of several methods, including cutting of the substrate with a laser, waterjet, or saw; planarization of the surface through methods such as polishing (see FIG. 6) or chemical or plasma etching; or physical removal of material such as that obtained in sputtering.

Fabrication of Reservoir Caps for Passive or Active Devices

In a preferred fabrication method, reservoir caps (either conducting or non-conducting) are formed via microinjection of a solution that contains the cap material in a solvent (see FIG. 7), or a suspension or slurry containing the cap material in a non-solvent. Yet another method of fabricating the reservoir caps or barrier layers is to microinject, in pure liquid form, the cap material. This method is applicable for materials with low melting points, which can easily be liquefied, and/or materials that will remain in liquid or gel form once they have been injected into the reservoirs (e.g., where it is desired to have a hydrogel cap on a reservoir).

Formation of the reservoir caps also can be accomplished by inkjet printing of a solution or slurry of the cap material, or of the cap material in pure liquid form, into the reservoirs. Reservoir caps also can be formed by spin coating of the cap material on the substrate, or by dipping the substrate (Jackman, et al., *Anal. Chem.* 70(11):2280–87 (1998)) in a liquid volume of the cap material, in its pure form, or in a solution or suspension.

Figure 10:
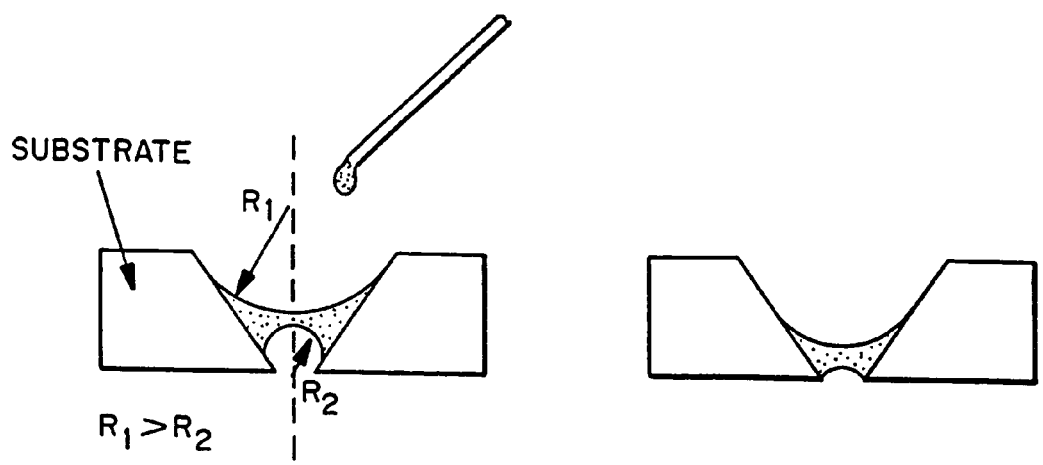
FIG. 10 illustrates one embodiment of a method for forming a reservoir cap in the substrate using capillary pressure.

For cap formation via microinjection or inkjet printing, capillary pressure pulls the liquid to the small end of the reservoir. The Young-Laplace equation offers a physical explanation of what happens to the liquid once it is injected into a reservoir. For the configuration shown in FIG. 10, the Young-Laplace equation is:

$$\Delta P = \gamma(2/R_2 - 2/R_1) \qquad \text{EQ. 1}$$

where $\Delta P$=the pressure difference (proportional to the stress) between the two sides of the interface, $\gamma$=surface tension of the liquid, and $R_1$ and $R_2$ are the radii of curvature of the droplet in the reservoir (see FIG. 10). Since the radius of curvature of the liquid is smaller on the side that touches the narrow end of the reservoir, there will be a corresponding pressure or stress that pulls the liquid in that direction. Thus, capillary action will drag the liquid to the narrow end of the reservoir and cause the cap to be formed therein.

For passive devices with metallic caps that would dissolve in certain environments, a thin foil of the desired metal can be attached to the substrate by application of pressure and/or an adhesive. A thin film or layer of metal may also be formed on the surface via e-beam evaporation, sputtering, chemical vapor deposition, or other deposition methods used for the fabrication of thin films or layers.

For some active devices, reservoir caps formed via microinjection or inkjet printing may serve as a support structure upon which outer, stimuli-responsive caps are formed. These inner, supporting caps are subsequently removed after the outer, responsive caps are formed. Alternatively, for an embodiment in which it is desired to have more than one cap per reservoir (for example, an outer electrically responsive cap and an inner cap that passively controls diffusion), the cap formed via microinjection may remain in place after the outer cap has been formed. Then, when the outer cap is removed, the inner cap controls the rate of release of the molecules from the reservoir by controlling diffusion out of the reservoir. Other embodiments of multi-layered or multi-component caps can be made by combining any number of disintegratable and non-disintegratable materials.

Fabrication of Release Systems for Passive or Active Devices

Release systems may be formed and deposited in reservoirs via the same methods described above for the reservoir caps. Namely, microinjection or inkjet printing of the release system materials in pure liquid form, gel form, solutions, suspensions, emulsions, or slurries. This includes combinations such as liquid excipient+solid release molecules=matrix slurry; solid excipient+liquid release molecules=matrix slurry; solid excipient+solid release molecules+solvent=solution of matrix materials; solid excipient+solid release molecules+non-solvent=matrix slurry; liquid excipient+liquid release molecules=pure liquid matrix.

Release systems may also be formed and deposited in reservoirs via spin coating of the substrate with the release materials in pure form, as a mixture, or as a solution, emulsion, slurry, or suspension, or dipping the substrate into a liquid volume of the release materials in pure, solution, or suspension form (discontinuous dewetting, described in Jackman, et al., *Anal. Chem.* 70(11):2280–87 (1998)).

Fabrication of Reservoir Caps and Circuitry for Active Devices

In a preferred embodiment, standard photolithography is used to pattern the conducting material (such as a polymer or metal) on the surface of the device into the desired configurations in order to form conducting caps over the reservoirs and circuitry on the surface of the device. E-beam evaporation, sputtering, chemical vapor deposition, metal lithography (Chou, et al., *Science*, 272:85–87 (1996)) or other deposition methods may be used to form metal reservoir caps as well as circuitry on the surface of the device.

Reservoir caps and conducting circuitry on the surface of the device can also be fabricated using microcontact printing and soft lithography methods, as described, for example, in Yan, et al., *J. Amer. Chem. Soc.*, 120:6179–80 (1998); Xia, et al., *Adv. Mater.*, 8(12):1015–17 (1996); Gorman, et al., *Chem. Mater.*, 7:52–59 (1995); Xia, et al., *Annu. Rev. Mater. Sci.*, 28:153–84 (1998); and Xia, et al., *Angew. Chem. Int. Ed.*, 37:550–75 (1998).

In a preferred embodiment, active release devices are provided with electrodes positioned in or near the reservoirs, such that upon application of an electric potential or current across or between the electrodes, the release system, for example one comprising a biodegradable polymeric matrix, (1) degrades due to local pH changes or (2) exchanges ions in solution with an ionically bound active substance, thereby releasing the molecules from the release system. The electrodes are formed by depositing a conducting material (such as a metal) on the substrate using standard microfabrication methods such as sputtering, followed by photolithographically patterning photoresist on the metal in the shape of the electrode, and then etching away the unmasked metal by wet etching. These microfabrication techniques are described, for example, in U.S. Pat. No. 5,797,898 and No. 6,123,861, to Santini, et al.

Figure 11:
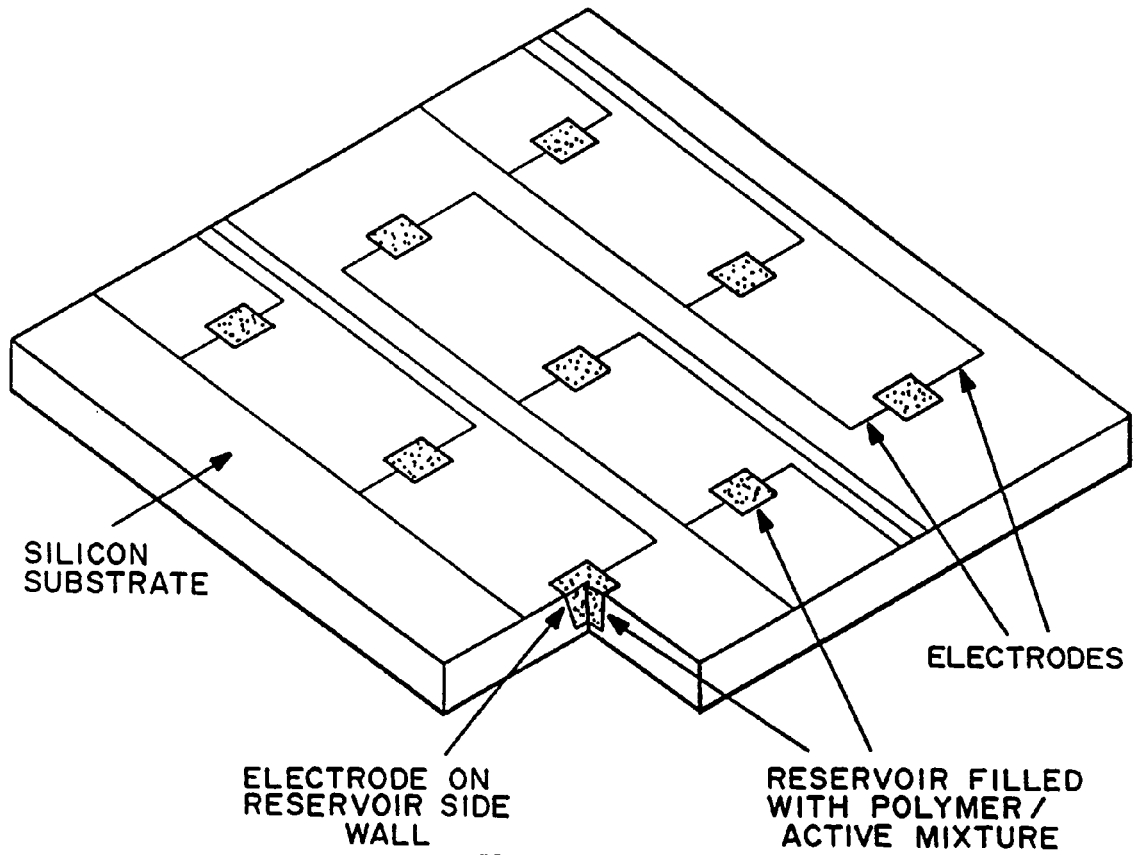
FIG. 11 is a schematic illustrating one embodiment of an active delivery device having electrodes on reservoir sidewalls.
Figure 12A:
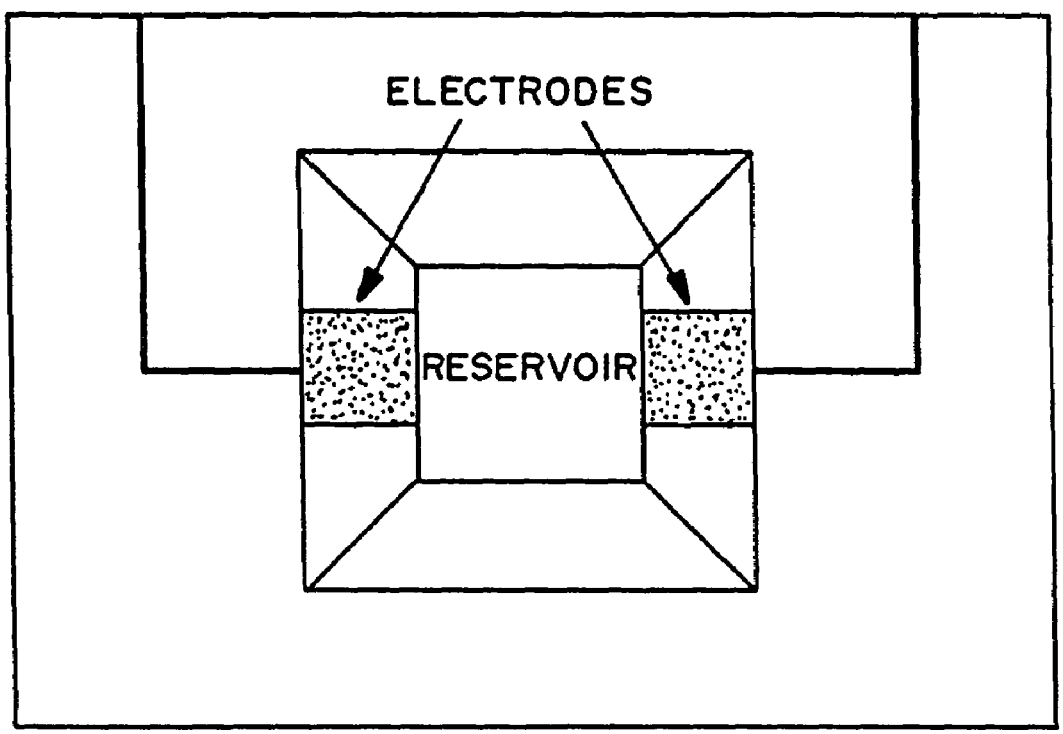
FIG. 12 is a top view (12a) and a cross-sectional side view (12b) of one embodiment of an active device having electrodes on reservoir sidewalls.
Figure 12B:
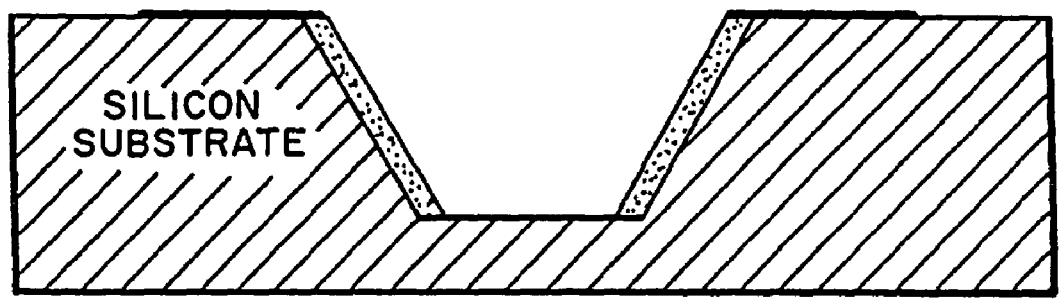

FIG. 11 and FIG. 12 illustrate one configuration in which the electrodes are fabricated on one or more surfaces of the reservoir. FIGS. 13$a$–$c$ illustrate how such a device can be activated to release the molecules from the release system upon application of an electric potential between or electric current through the electrodes. FIG. 13$b$ shows a polymer/active agent matrix wherein the polymer degrades upon application of the electric current through the electrodes. FIG. 13$c$ shows a polymer/active agent matrix wherein the polymer undergoes ion exchange upon application of the electric current.

Removal of the Reservoir Cap from Active Devices

For some configurations of active devices, (inner) reservoir caps formed via microinjection or inkjet printing may serve as supporting structures upon which (outer) stimuli-responsive, reservoir caps are formed. The inner reservoir caps optionally can be removed following formation of the outer reservoir caps. Alternatively, the inner reservoir caps may serve both as supporting and release controlling structures, which remain in the reservoirs after the outer reservoir caps are formed. The inner reservoir caps can control the release profile of the molecules by disintegration or diffusion, after the outer reservoir caps have been removed or made permeable.

For applications in which it is desired to remove the reservoir cap from underneath the conducting caps, this step generally must be completed before the reservoir is filled with the molecules to be released. Removal of the cap or barrier layer may be accomplished, for example, by either an ion beam or reactive ion plasma, or by chemical etching.

Reservoir Filling

The release system containing the molecules for delivery is inserted into one of the openings of the reservoir by injection (microinjection) or inkjet printing. Each reservoir can contain different molecules and/or a different dosage. Similarly, the release kinetics of the molecules in each reservoir can be varied by the choice of reservoir cap configuration and materials and release system composition. In addition, the mixing or layering of release system and cap materials in each reservoir can be used to tailor the release kinetics to the needs of a particular application.

The distribution over the microchip of reservoirs filled with the release system containing the molecules to be delivered can vary depending on the medical needs of the patient or other requirements of the system. For applications in drug delivery, for example, the drugs in each of the rows can differ from each other. Also, the release system or materials comprising the release system can differ within each row to release the drug at different rates and times from different reservoirs. The dosages can also vary within each row. Differences in reservoir loading can be achieved by injection or inkjet printing of different amounts of material directly into each reservoir. Although injection and inkjet printing are the preferred methods of filling reservoirs, it is understood that each reservoir can be filled individually by capillary action, by pulling or pushing the material into the reservoir using a vacuum or other pressure gradient, by melting the material into the reservoir, by centrifugation and related processes, by manually packing solids into the reservoir, by spin coating, or by any combination of these or similar reservoir-filling techniques. FIG. 8 illustrates filling of reservoirs with release system via microinjection.

Device Packaging, Control Circuitry, and Power Source

Figure 9E:
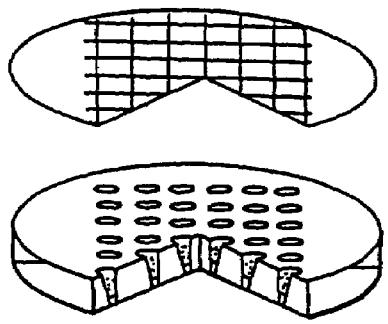
Figure 9F:
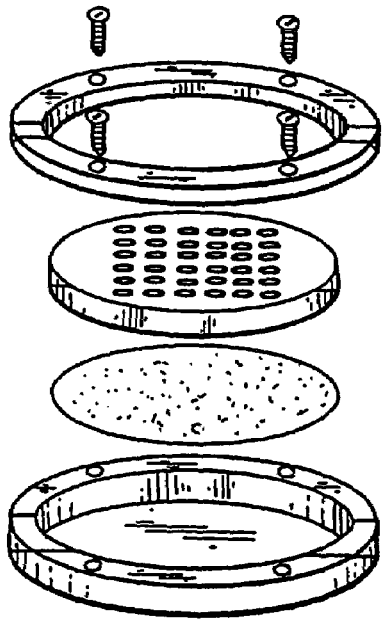

After the molecules to be released have been inserted into the reservoirs, the backside of the device (side with open ends of reservoirs into which the release systems and molecules have been placed) is sealed with a material or combination of materials that are impervious to the surrounding medium. Examples of these materials include waterproof, thermally- or UV-curable epoxies; spray adhesives; glass microscope slides and cover glasses; silicon; ceramics; rubbers; and polymeric materials such as poly (tetrafluoroethylene) or poly(caprolactone). FIG. 9 illustrates sealing a microchip using a microslide glass cover secured with an adhesive spray, for in vitro applications. Other examples of sealing methods also are shown in FIG. 9. For embodiments in which the entire device is desired to be biodegradable, the sealant material must have a degradation time that is greater than the longest release time of the molecules in the device, in order to prevent dose dumping or leaking of the molecules through the degraded sealant material.

Control over the release rate and time of molecules from the passive devices is based upon the design and fabrication of the device, for example the reservoir cap materials and thicknesses, release system compositions, or size of reservoir openings. Thus no control circuitry or power source is necessary for the passive devices.

Further details on packaging, control circuitry, and power sources for the active devices are described in U.S. Pat. No. 5,797,898 and No. 6,123,861, to Santini, et al.

In one embodiment, the microchip device is surface modified (e.g., coated) to provide a desired functionality, such as to enhance biocompatability or bioadhesion using techniques known in the art. It is generally preferred that the release mechanism (i.e., release from the reservoirs) of the microchip device not be altered by the surface modification.

III. Applications for Using the Microchip Devices

Passive and active devices have numerous in vivo, in vitro, and commercial diagnostic applications. The microchips are capable of delivering precisely metered quantities of molecules and thus are useful for in vitro applications, such as analytical chemistry and medical diagnostics, as well as biological applications such as the delivery of factors (e.g., growth factors and regulating factors) to cell cultures. In other applications, the devices are used to control release of fragrances, dyes, reagents, or other useful chemicals.

In one embodiment, the microchip devices can be used in vivo for the delivery of drugs to humans and animals. The microchips are especially useful for drug therapies in which it is desired to control the exact amount, rate, and/or time of delivery of the drug. Due to the small size of these devices, preferred drug delivery applications include the delivery of potent compounds such as hormones, steroids, chemotherapy medications, gene therapy compounds and vectors, and some strong painkillers, as the amount of the molecules that may be stored in the devices is relatively small. The microchips can be implanted via surgical procedures or injection, or swallowed, and can deliver many different drugs, at varying rates and varying times.

The present invention will be further understood with reference to the following non-limiting examples.

EXAMPLE 1

Fabrication of Polymeric Microchip Device Having Cholesterol Reservoir Caps

The following procedure was used to produce a polymeric microchip device having cholesterol reservoir caps for passive release.

Figure 4A:
FIGS. 4a–f illustrate a preferred method of molding a partially dense (4d) and a completely dense (4f) polymer preform.
Figure 5:
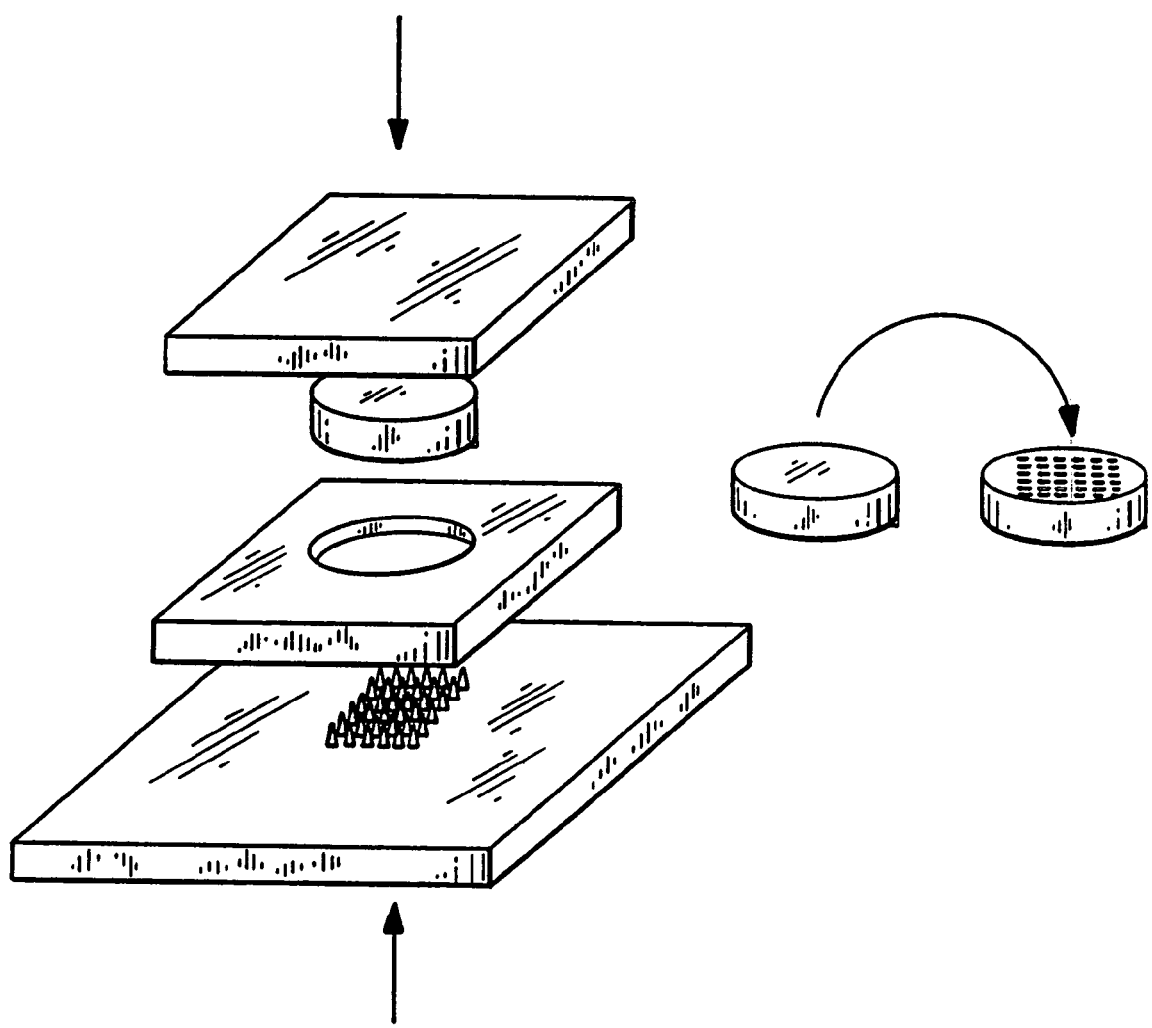
FIG. 5 illustrates one embodiment of a molding step for forming reservoirs in a polymeric device.

(1) Weighed 0.4 g of poly(lactic-co-glycolic acid) powder, molecular weight 25,000 powder (see FIG. 4*a*).

Figure 4B:
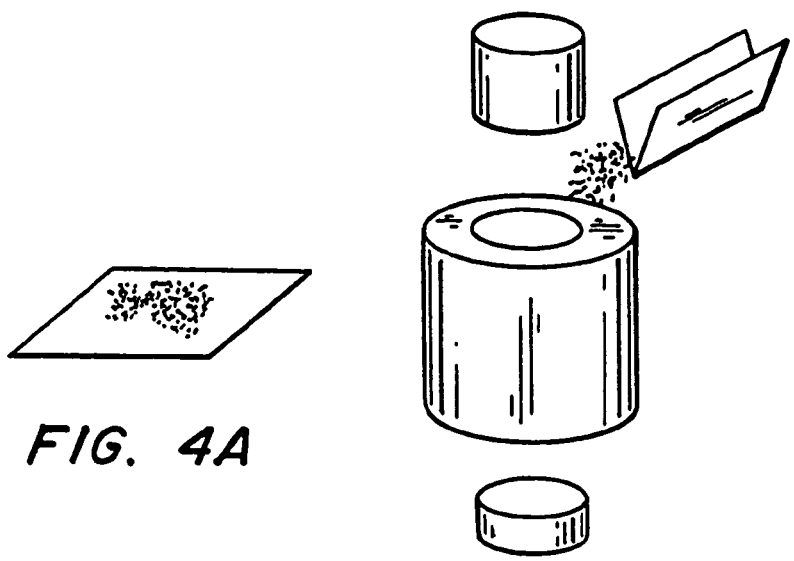
Figure 4C:
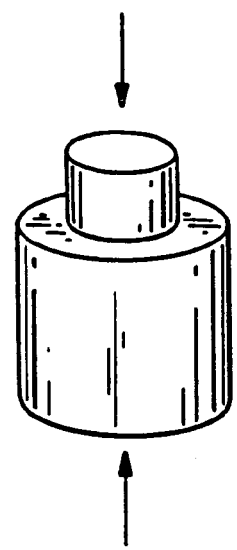

(2) Inserted bottom piston into conical steel die, 1.27 cm (½") in diameter, filled with polymer powder from step (1), and inserted top piston into die (see FIG. 4*b*).

(3) Put the die with powder into Carver Laboratory Press, model C. Pressed at room temperature for one minute and thirty seconds at approximately $69 \times 10^6$ Pa (10,000 psi), yielding a cylindrical polymer preform (see FIG. 4*c*).

Figure 4D:
Figure 4E:
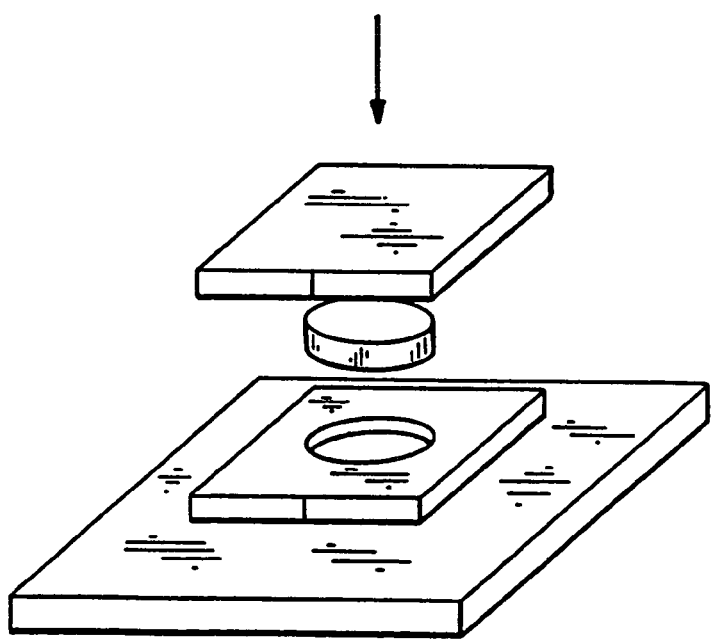
Figure 4F:

(4) Removed cylindrical polymer preform from the die (see FIG. 4*d*).

(5) Placed cylindrical polymer preform into aluminum die plate (aluminum sheet, approximately 3 mm (or ⅛") thick, with a hole of approximately the same diameter as the polymer preform). Allowed die plate to rest on Teflon sheet, approximately 1.6 mm thick (1/16"), and covered top with another aluminum plate, 3 mm (or ⅛") thick (see FIG. 4*e*).

(6) Placed the assembly from (5) into Carver Laboratory Press, model C, at 104° C. (220° F.). Set temperature of heated platens to about 54° C. (130° F.). As the polymer preform melted, the platens were slowly brought together. The load pressure remained between 0 and 4448 N (1000 pounds-force). The assembly was left in the lab press until the platens cooled to 54° C. (130° F.), approximately one to one and a half hours.

(7) Removed the assembly from the lab press. The assembly was further cooled by running under cool water (see FIG. 4*f*).

(8) Placed aluminum die plate (with densified polymer preform in it) on top of aluminum indenter plate, containing an array of indenters for forming the reservoirs in the polymeric substrate. Covered the top of aluminum die plate with another aluminum plate, 3 mm thick (see FIG. 5).

(9) Placed the assembly into Carver Lab Press, Model C, at 54° C. (130° F.). As polymer preform remelted, the platens were brought together and pressure slowly applied until pressure gauge read between 11120 and 13344 N (2500 and 3000 pounds-force). Hot pressed the preform in this manner for 20 minutes, which formed reservoirs in the polymeric substrate. A hole machined in the side of the indenter plate allowed monitoring of the temperature close to the polymer preform. A T-type thermocouple connected to an Omega HH21 microprocessor thermometer was used.

(10) Removed the assembly from Lab Press and allowed it to cool in ambient air to approximately 32° C. (90° F.).

(11) Removed indented polymer preform, i.e. the substrate, from aluminum indenter and die plates.

(12) Attached the indented polymer preform to suitable mount using an adhesive. Double-sided tape was used to affix the indented polymer preform to a cylindrical brass block, approximately 3.81 cm (1½") in diameter and approximately 1.27 to 3.81 cm (½" to 1½") tall (see FIG. 6a). Ensured that the indented side of the preform was facing the mount. Alternatively, a multiple-mount polishing fixture similar to those available commercially may be used to hold the samples during polishing.

Figure 6B:
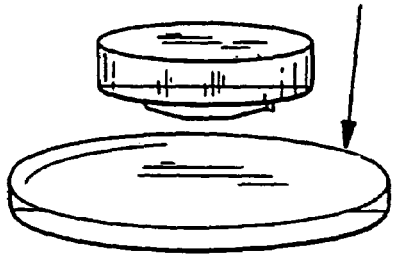
Figure 6C:
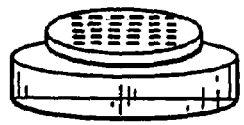

(13) Polished the substrate using Buehler Ecomet IV Rotary Polisher, until ends of reservoirs were exposed (see FIG. 6b and FIG. 6c). Substrate was checked frequently to monitor the progress of the polishing. Typical polishing procedure with ranges of polishing times are shown in Table 1.

TABLE 1

Polishing Materials and Procedures

| Type of Paper | Paper Grit | Polisher Speed | Media | Polishing Time (range in min:sec) |
|---|---|---|---|---|
| Buehler Carbimet Silicon Carbide Grinding Paper | 400 | 250 rpm | water | 4:30–6:00 |
| | 600 | 250 rpm | water | 1:00–3:00 |
| Buehler Microcut Silicon Carbide Grinding Paper | 800(P2400) | 250 rpm | water | 0:30–2:00 |
| | 1200(P4000) | 250 rpm | water | 0:30–1:30 |

(14) Removed the substrate from the mount. A solvent may be used to loosen the adhesive and aid substrate removal from the mount. For substrates mounted with double sided tape on brass blocks, soaking of the substrate in ethanol for 5 to 20 minutes was found to loosen the adhesive.

(15) Mixed desired solutions for formation of reservoir caps (e.g., solutions of 5, 10, 15, and 20 weight % cholesterol in chloroform were used). Gently mixed the solution with a magnetic stir plate and magnetic stirrer bar for at least five minutes. Cholesterol was utilized because it is known to be biocompatible, dissolvable, and resorbable in vivo.

(16) Filled a Becton-Dickinson 1 mL plastic syringe (item #309602) with desired cap solution.

(17) Attached a World Precision Instruments MicroFil™ Flexible needle (item #MF34G-5) to syringe.

(18) Inserted MicroFil™ needle into end of a Unimetrics 10 μL Luer Lock glass syringe (World Precision Instruments item #14392), opposite plunger.

(19) Depressed plunger on 1 mL plastic syringe, filling 10 μL glass syringe with cap solution.

(20) Removed MicroFil™ needle from glass syringe.

(21) Placed end of MicroFil™ needle in reservoir end of Hamilton instruments 32 gauge needle (item #91032). Depressed plunger on plastic 1 mL syringe in order to fill needle reservoir with cap solution, which minimized formation of air bubbles when needle was attached to glass syringe.

(22) Attached 32 gauge needle to 10 μL glass syringe.

(23) Placed 10 μL glass syringe assembly into syringe chamber on World Precision Instruments microinjector (item #UMP-G).

(24) Placed the substrate to be injected on glass slide assembly, with one end of reservoirs facing up and the edges of the device resting on the glass slides. Ensured that ends of reservoirs on opposite side were not resting on a surface. Tape was used to hold substrate in place on glass slides.

(25) Entered desired total injection volume and volume flow rate on World Precision Instruments Micro 1™ Microsyringe Pump Controller (typical volumes were between about 20 and 200 nL, at a flow rate of 20 nL/sec).

Figure 7A:
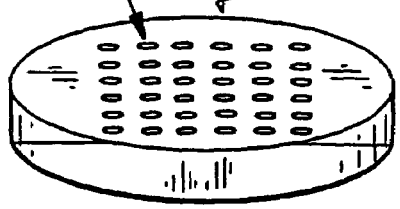
FIGS. 7a–b illustrate one embodiment of a method for forming reservoir caps in the substrate via microinjection.

(26) Tilted microinjector assembly and aligned needle tip with rows of reservoirs (see FIG. 7a).

(27) Using fine control knobs, placed needle tip in reservoir into which cap solution was to be injected.

(28) Depressed "Run" button to inject desired volume into reservoir.

(29) Using fine control knobs on microinjector, removed needle from reservoir and moved to next reservoir to be injected.

Figure 7B:
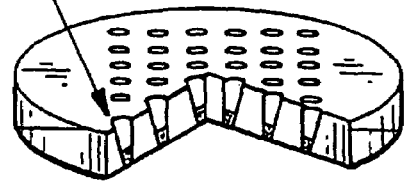

(30) Repeated steps (26) through (29) until all desired reservoirs were filled with cap solution (see FIG. 7b).

(31) Removed 10 μL glass syringe from microinjector.

Figures 8A, 8B:
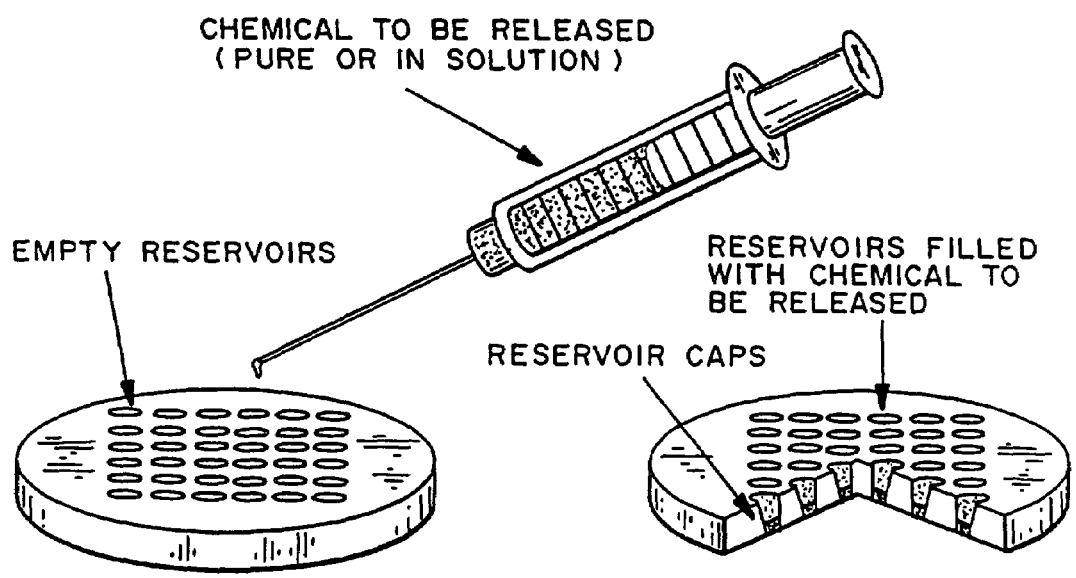
FIGS. 8a–b illustrate one embodiment of a method for forming release systems in the substrate via microinjection.

(32)–(47) Repeated steps (15) through (30) for release systems (pure liquid molecules or mixture of molecules and excipient) (see FIG. 8a and FIG. 8b). Here, the release system used was deionized water containing approximately 10 mM concentration of sodium flourescein, and approximately 20% by volume of poly(ethylene glycol), having a molecular weight of 200. Approximately 20 nL of this solution was injected, at an injection rate of 20 nL/s, into each reservoir from which it was desired to release the fluorescein. Separate syringes were used for cap solutions and release system solutions to avoid contamination.

(48) Sprayed microcover glass (VWR Brand Micro Cover Glass, Square, No. 1, 22 mm square×0.13–0.17 mm thick, VWR item #48366–067), with 3M Super 77 Spray Adhesive. Waited until adhesive became tacky (see FIG. 9).

(49) Using tweezers, placed polymer device on micro cover glass (or other suitable covering material). The injected side of the substrate contacted the cover, leaving the reservoir caps accessible, and thereby sealing the microchip device.

(50) Allowed the adhesive to dry. The microchip device was then ready for use (see FIG. 9).

EXAMPLE 2

Fabrication of Polymeric Microchip Device Having Cholesterol/Lecithin Reservoir Caps The following alternative procedure was used to produce a polymeric microchip device having cholesterol/lecithin reservoir caps for passive release.

(1)–(4) Followed steps (1) through (4) described in Example 1 to form a polymer preform.

(5) Placed cylindrical polymer preform into aluminum die plate (aluminum sheet, approximately 3 mm (or ⅛") thick, with a hole of approximately the same diameter as the polymer preform). Allowed die plate to rest on aluminum plate having conical indenters, and covered top with another aluminum plate, 3 mm (or ⅛") thick.

(6) Placed the assembly from (5) into Carver Laboratory Press, model C, at 54° C. (130° F.). Set temperature of heated platens to 54° C. (130° F.). The load pressure remained at approximately 8896 N (2000 pounds-force). The assembly was left in the lab press for approximately ten minutes. A hole machined in the side of the indenter plate allowed monitoring of the temperature close to the polymer preform. A T-type thermocouple connected to an Omega HH21 microprocessor thermometer was used.

(7) Removed the assembly from Lab Press and allowed it to cool in ambient air to approximately 32° C. (90° F.).

(8) Removed indented polymer preform, i.e. the substrate, from aluminum indenter and die plates.

(9) Attached indented polymer preforms to suitable mounts using an adhesive. Double-sided tape was used to affix the indented polymer preforms to cylindrical polymer blocks, approximately 2.54 cm (1") in diameter and approximately 2.54 cm (1") tall. Ensured that the indented sides of the preforms were facing the mount.

(10) Loaded the mounted substrates into a multiple sample holder (Buehler item 60–5160, Controlled Material Removal Accessory) and set diamond stops to desired thickness of material to be removed (typically 1.32 mm or 0.052"). (11) Loaded sample holder into Buehler Ecomet IV Rotary Polisher, and polished substrates until ends of reservoirs were exposed/surface of samples became level with diamond stops. Substrates were checked frequently to monitor the progress of the polishing. Typical polishing procedures with ranges of polishing times are shown in Table 2.

TABLE 2

Polishing Materials and Procedures

| Type of Paper | Paper Grit | Polisher Speed | Media | Polishing Time (range in min:sec) |
|---|---|---|---|---|
| Buehler Carbimet Silicon Carbide Grinding Paper | 320 | 250 rpm | water | 4:30–6:00 |
| | 600 | 250 rpm | water | 1:00–3:00 |
| Buehler Microcut Silicon Carbide Grinding Paper | 1200(P4000) | 250 rpm | water | 0:30–1:30 |

(12) Followed step (14) described in Example 1 to remove the substrate from the mount.

(13) Mixed desired solutions for formation of reservoir caps (e.g., solutions of 2 wt. % cholesterol and 3 wt. % lecithin (which is a crystallization inhibitor for cholesterol) in a mixture of chloroform and ethanol). Gently mixed the solution with a magnetic stir plate and magnetic stirrer bar for at least 5 minutes.

(14)–(29) Followed steps (16) through (31) described in Example 1 to form reservoir caps.

(30)–(45) Repeated steps (14) through (29) for release systems (pure liquid molecules or mixture of molecules and excipient). In this case, the release system used was deionized water with approximately 13 mM concentration of sodium fluorescein. Approximately 20 nL of the release system was injected, at an injection rate of 205 nL/sec, into each reservoir from which it was desired to release fluorescein. Separate syringes were used for cap solutions and release system solutions to avoid contamination.

(46) Mixed Master Bond EP30HTF epoxy according to directions.

(47) Using a toothpick, coated one side of rubber o-ring (Greene Rubber Company, item # 2-001 $N_{0674}$-70 BUNA-N O-RING) with epoxy, and placed o-ring on surface of substrate (side of microchip device opposite reservoir caps). Repeated step for each reservoir filled with release system.

(48) Let epoxy dry for at least four hours.

(49) Mixed another batch of Master Bond EP30HTF epoxy according to directions, and then coated thin layer of epoxy on backside of microchip device over all areas outside of o-rings.

(50) Let epoxy dry for at least four hours.

(51) Mixed a further batch of Master Bond EP30HTF epoxy according to directions; coated a thin layer of epoxy on top surface of o-rings; and affixed glass microscope slide to top of o-rings, sealing the microchip device.

(52) Allowed the epoxy dry for at least 24 (preferably 48) hours. The microchip device was then ready for use.

EXAMPLE 3

Fabrication of Polymeric Microchip Device Having Polymeric Reservoir Caps

The following procedure was used to produce a polymeric microchip device having polyester reservoir caps for passive release.

(1) Weighed desired amount of a polymer powder (see FIG. 4a). Here, 0.4 g of poly(lactic acid) (MW approximately 100,000) was used.

(2) Inserted bottom piston into conical steel die, 1.27 cm (½ inch) in diameter, filled die with polymer powder from step (1), and inserted top piston into die (see FIG. 4b).

(3) Placed the die with powder into Carver Laboratory Press, model C. Pressed at room temperature for one minute and thirty seconds at approximately $69 \times 10^6$ Pa (10,000 psi), yielding a cylindrical polymer preform (see FIG. 4c).

(4) Removed cylindrical polymer preform from the die (see FIG. 4d).

(5) Placed polymer preform on aluminum die plate containing an array of indenters for forming the reservoirs in the polymeric substrate. An aluminum plate 3 mm thick, with a 1.27 cm (½") diameter hole in it, was placed on top of the indenter plate so that the polymer preform was sitting in the hole of the plate. Covered the top of this aluminum plate with another aluminum plate, 3 mm thick (see FIG. 5).

(6) Placed the assembly into Carver Lab Press, Model C, at 182° C. (360° F.). Platens were brought together and pressure slowly applied until pressure gauge read between 4448 and 8896 N (1000 and 2000 pounds-force). Hot pressed the preform in this manner for 15 minutes, which formed reservoirs in the polymeric substrate. A hole machined in the side of the indenter plate allowed monitoring of the temperature close to the polymer preform. A T-type thermocouple connected to an Omega HH21 microprocessor thermometer was used.

(7) Removed the assembly from Lab Press and allowed it to cool in ambient air to approximately 32° C. (90° F.).

(8) Removed indented polymer preform, i.e. the substrate, from aluminum indenter and die plates.

(9) Attached indented polymer preforms to suitable mounts using an adhesive. Double-sided tape was used to affix the indented polymer preforms to cylindrical polymer blocks, approximately 2.54 cm (1") in diameter and approximately 2.54 cm (1") tall. Ensured that the indented sides of the preforms were facing the mount.

(10) Loaded the mounted substrates into a multiple sample holder (Buehler item 60-5160, Controlled Material Removal Accessory) and set diamond stops to desired thickness of material to be removed (typically 1.32 mm or 0.052").

(11) Loaded sample holder into Buehler Ecomet IV Rotary Polisher, and polished substrates until ends of reservoirs were exposed/surface of samples became level with diamond stops. Substrates were checked frequently to monitor the progress of the polishing. Typical polishing procedure with ranges of polishing times are shown in Table 3.

TABLE 3

Polishing Materials and Procedures

| Type of Paper | Paper Grit | Polisher Speed | Media | Polishing Time (range in min:sec) |
|---|---|---|---|---|
| Buehler Carbimet Silicon Carbide Grinding Paper | 240 | 250 rpm | water | 1:00–3:00 |
| | 600 | 250 rpm | water | 1:00–3:00 |
| Buehler Microcut Silicon Carbide Grinding Paper | 1200(P4000) | 250 rpm | water | 0:30–1:30 |

(12) Removed the substrate from the mount. A solvent may be used to loosen the adhesive and aid substrate removal from the mount. For substrates mounted with double sided tape on brass blocks, soaking of the substrate in ethanol for 5 to 20 minutes loosened the adhesive.

(13) Mixed desired solutions for formation of reservoir caps (e.g., solutions of 5 to 10 vol. % of poly(L-lactic-co-glycolic acid), molecular weight of approximately 25,000, in dichloromethane). Gently mixed the solution with a magnetic stir plate and magnetic stirrer bar for at least 5 minutes.

(14) Filled a Becton-Dickinson 1 mL plastic syringe (item #309602) with desired cap solution.

(15) Attached a World Precision Instruments MicroFil™ Flexible needle (item #MF34G-5) to syringe.

(16) Inserted MicroFil™ needle into end of a Unimetrics 50 µL Luer Lock glass syringe (World Precision Instruments item #15895), opposite plunger.

(17) Depressed plunger on 1 mL plastic syringe, filling 50 µL glass syringe with cap solution.

(18) Removed MicroFil™ needle from glass syringe.

(19) Placed end of MicroFil™ needle in reservoir end of Hamilton instruments 32 gauge needle (item #91032). Depressed plunger on plastic 1 mL syringe in order to fill needle reservoir with cap solution, which minimized formation of air bubbles when needle was attached to glass syringe.

(20) Attached 32 gauge needle to 50 µL glass syringe.

(21) Placed 50 µL glass syringe assembly into syringe chamber on World Precision Instruments microinjector (item #UMP-G).

(22) Placed the substrate to be injected on glass slide assembly, with one end of reservoirs facing up and the edges of the device resting on the glass slides. Ensured that ends of reservoirs on opposite side were not resting on a surface. Tape was used to hold substrate in place on glass slides.

(23) Entered desired total injection volume and volume flow rate on World Precision Instruments Micro 1™ Microsyringe Pump Controller (typically multiple injections of 100–200 nL will be done at a flow rate of 205 nL/sec).

(24) Tilted microinjector assembly and aligned needle tip with rows of reservoirs (see FIG. 7a).

(25) Using fine control knobs, placed needle tip in reservoir into which cap solution was to be injected.

(26) Depressed "Run" button to inject desired volume into reservoir.

(27) Using fine control knobs on microinjector, removed needle from reservoir and moved to next reservoir to be injected.

(28) Repeated steps (25) through (27) until all desired reservoirs were filled with cap solution (see FIG. 7b).

(29) Removed 50 µL glass syringe from microinjector.

(30)–(45) Repeated steps (13) through (28) for release systems (pure liquid molecules or mixture of molecules and excipient) (see FIG. 8a and FIG. 8b). The release system used was deionized water containing approximately 13 mM concentration of sodium flourescein, and 20 nL of this solution was injected, at an injection rate of 205 nL/s, into each reservoir from which it is desired to release fluorescein. Used separate syringes for cap solutions and release system solutions to avoid contamination.

(46) Mixed Master Bond EP30HTF epoxy according to directions.

(47) Using a toothpick, coated one side of rubber o-ring (Greene Rubber Company, item # 2-001 N0674-70 BUNA-N O-RING) with epoxy, and placed o-ring on surface of substrate (side of microchip device opposite reservoir caps). Repeated step for each reservoir filled with release system.

(48) Let epoxy dry for at least four hours.

(49) Mixed another batch of Master Bond EP30HTF epoxy according to directions, and then coated thin layer of epoxy on backside of microchip device over all areas outside of o-rings.

(50) Let epoxy dry for at least four hours.

(51) Mixed a further batch of Master Bond EP30HTF epoxy according to directions, and coated a thin layer of epoxy on top surface of o-rings, and affixed glass microscope slide to top of o-rings, sealing the microchip device.

(52) Let epoxy dry for at least 24 (preferably 48) hours. The microchip device was then ready for use.

EXAMPLE 4

Fabrication of Ceramic Microchip Device Having Cholesterol Reservoir Caps

The following procedure is one that can used to produce ceramic microchip devices having cholesterol reservoir caps for passive release.

(1) Weigh out desired amount of ceramic powder or measure a desired amount of a slurry containing the ceramic.

(2) Compression mold the ceramic powder, or cast the slurry, at room temperature with an indenter plate to form partially dense, reservoir-containing substrate.

(3) Densify the substrate of step (2) via sintering at high temperature.

(4)–(6) Polish the substrate as described in steps (12) through (14) of Example 1. Polishing grits, speeds, and times will vary from those used for the polymer devices.

(7)–(23) Form reservoir caps via microinjection of cap solution as described in steps (15) through (31) of Example 1.

(24)–(39) Fill reservoirs with release system via microinjection as described in steps (32) through (47) of Example 1.

(40–46) Seal microchip as described in steps (46) through (52) of Example 2.

EXAMPLE 5

Fabrication of Polymeric Microchip Device for Active Release, Using Microinjection and Photolithography The following procedure can be used to produce polymeric microchip devices for active release.

(1)–(31) Follow steps (1) through (31) of Example 1 to form polymeric substrate having reservoirs and reservoir caps.

(32) Using standard microfabrication techniques, pattern an electrically erodible polymer, such as a complex of poly(ethyloxazoline) and poly(methacrylic acid), reservoir cap material over the desired regions of the substrate, which includes the area over the reservoir openings. This would typically involve:
  (a) spin coating of the polymer and a photoresist;
  (b) photolithography to expose and develop the photoresist;
  (c) removal of the polymer from specified regions of the substrate surface (excluding regions protected by photoresist) via methods such as chemical, plasma, or ion beam etching;
  (d) removal of the photoresist from the remaining areas of the substrate; and
  (e) optional removal of the inner reservoir cap (underneath the conducting polymer cap) by etching the backside of the substrate via chemical, plasma, or ion etching.

(33)–(48) Fill with the reservoirs with the molecules to be released as described in steps (15) through (30) of Example 1.

(49)–(55) Seal the microchip device as described in steps (46) through (52) of Example 2.

EXAMPLE 6

Fabrication of Ceramic Microchip Device for Active Release, Using Microinjection and Photolithography The following procedure is one that can be used to produce ceramic microchip devices for active release.

(1)–(6) Follow steps (1) through (6) of Example 4 to form and polish the ceramic substrate.

(7)–(22) Fabricate reservoir caps via microinjection as described in steps (32) through (47) of Example 1.

(23) Pattern electrically conducting material to form electrical circuitry and conducting caps over reservoirs as described in step (32) of Example 5.

(24)–(39) Fill reservoirs with release systems via microinjection as described in steps (32) through (47) of Example 1.

(40)–(46) Seal microchip device as described in steps (46) through (52) of Example 2.

EXAMPLE 7

Fabrication of Polymeric Microchip Device for Active Release, Using Microinjection and Microcontact Printing The following is another procedure that can be used to produce polymeric microchip devices for active release.

(1)–(30) Follow steps (1) through (30) of Example 1 to form polymeric substrate having reservoirs and inner reservoir caps.

(31) Pattern conducting circuitry and outer reservoir caps onto inner reservoir caps using standard microcontact printing methods. See, for example, Gorman, et al., *Chem. Mater.*, 7:526–529 (1995); Xia et al., *Adv. Mater.*, 8:1015:1017 (1996); Yan et al., *J. Am. Chem. Soc.*, 120:6179–6180 (1998); Marzolin et al., *Thin Solid Films*, 315:9–12 (1998).

(32) If desired, remove inner reservoir caps from under outer reservoir caps using etching methods, as described in step (32e) of Example 5.

(33)–(48) Fill the reservoirs with the molecules to be released as described in steps (32) through (47) of Example 1.

(49)–(55) Seal the microchip device as described in steps (46) through (52) of Example 2.

EXAMPLE 8

Fabrication of Ceramic Microchip Device for Active Release Using Microinjection and Microcontact Printing The following is another procedure that can be used to produce ceramic microchip devices for active release.

(1)–(6) Follow steps (1) through (6) of Example 4 to form and polish the ceramic substrate.

(7)–(23) Fabricate reservoir caps via microinjection as described in steps (15) through (31) of Example 1.

(24) Pattern conducting circuitry and outer reservoir caps onto inner reservoir caps using standard microcontact printing methods.

(25) If desired, remove inner reservoir caps from under outer reservoir caps using etching methods as described in step (32e) of Example 5.

(26)–(41) Fill with the molecules to be released as described in steps (32) through (47) of Example 1.

(42)–(48) Seal the microchip device as described in steps (46) through (52) of Example 21.

Publications cited herein and the material for which they are cited are specifically incorporated by reference. Nothing herein is to be construed as an admission that the invention is not entitled to antedate such disclosure by virtue of prior invention.

Modifications and variations of the methods and devices described herein will be obvious to those skilled in the art from the foregoing detailed description. Such modifications and variations are intended to come within the scope of the appended claims.

We claim:

1. A device for use in medical diagnostics comprising:
   a substrate;
   an array of reservoirs in the substrate, the reservoirs having interior sidewalls, a closed bottom surface, and an opening distal the bottom surface;
   a plurality of electrodes located at least partially inside the reservoirs;
   a plurality of discrete reservoir caps covering the openings in the reservoirs; and
   control circuitry for selectively disintegrating or permeabilizing the reservoir cap over the opening of at least one of the reservoirs.

2. The device of claim 1, further comprising a diagnostic reagent in the interior of the reservoirs.

3. The device of claim 1, wherein the electrodes are located on sidewalls of the reservoirs.

4. The device of claim 1, wherein the electrodes comprise a thin film of a conducting metal or doped semiconductor.

5. The device of claim 1, wherein the reservoir caps comprise a metal.

6. The device of claim 1, wherein the substrate comprises silicon.

7. The device of claim 1, wherein the control circuitry is adapted to deliver an electric curt or potential to the reservoir cap effective to cause the reservoir cap to disintegrate.

8. The device of claim 1, further comprising an inner cap beneath the reservoir cap and in the opening, for passively controlling transport of molecules through the reservoir opening via diffusion of molecules through the inner cap.

9. The device of claim 8, wherein the inner cap comprises a polymeric material.

10. The device of claim 1, wherein the device is formed or coated with a biocompatible material, the device being suitable for implantation into a human or animal.

11. The device of claim 1, further comprising a glucose sensitive material in the interior of the reservoirs.

12. An implantable medical device for in vivo medical diagnostics comprising:
    a substrate;
    an array of reservoirs in the substrate, the reservoirs having interior sidewalls, a closed bottom surface, and an opening distal the bottom surface;
    a diagnostic reagent in the interior of the reservoirs;
    a plurality of electrodes located at least partially inside the reservoirs;
    a plurality of discrete reservoir caps covering openings in the array of reservoirs; and
    control circuitry for selectively disintegrating the reservoir cap over the opening of at least one of the reservoirs,
    wherein the device is formed or coated with a biocompatible material and is suitable for implantation into a human or animal.

13. The device of claim 12, wherein the electrodes are located on sidewalls of the reservoirs.

14. The device of claim 12, wherein the electrodes comprise a thin film of a conducting metal or doped semiconductor.

15. The device of claim 12, wherein the reservoir caps comprise a metal film.

16. The device of claim 12, wherein the substrate comprises silicon.

17. The device of claim 12, wherein the control circuitry is adapted to deliver an electric current or potential to the reservoir cap effective to cause the reservoir cap to disintegrate.

18. The device of claim 12, further comprising an inner cap beneath the reservoir cap and in the opening, for passively controlling transport of molecules through the reservoir open diffusion of molecules through the inner cap.

19. The device of claim 18, wherein the inner cap comprises a polymeric material.

20. A device for the controlled delivery of molecules comprising:
    a substrate;
    an array of reservoirs in the substrate;
    a release system in the reservoirs comprising molecules for release;
    one or more electrodes attached to the substrate at least partially inside the reservoirs, wherein the one or more electrodes are not reservoir caps; and
    means for applying an electric current or potential across the one or more electrodes effective to activate release of the molecules from the reservoirs.

21. The device of claim 20, wherein the device is formed of or coated with a biocompatible material suitable for implantation into a human or animal.

22. The device of claim 20, wherein the release system comprises a matrix material and the molecules for release comprise drug molecules, which are dispersed in the matrix material.

23. The device of claim 22, wherein the matrix material comprises a biodegradable polymer.

24. The device of claim 22, wherein the matrix material disintegrates due to local pH changes induced by application of the electric potential or current.

25. The device of claim 22, wherein, upon application of the electric potential or current, the matrix material exchanges ions in solution with an ionically bound active substance in the release system.

26. The device of claim 20, further comprising reservoir caps positioned over the release system, wherein release of the molecules is controlled by diffusion through or disintegration of the reservoir caps.

27. The device of claim 26, wherein application of the electric current or potential across the one or more electrodes swells the release system to rupture the reservoir cap and release the molecules.

28. The device of claim 26, wherein the reservoir caps are outer reservoir caps, and the device further comprises inner reservoir caps positioned the reservoirs beneath the outer reservoir caps, wherein the inner reservoir caps are permeabilized or disintegrated to release the molecules after the outer reservoir caps are permeabilized or disintegrated.

29. The device of claim 26, wherein the reservoir caps are outer reservoir caps and the release system is a first release system layer, and the device further comprises at least one additional release system layer and at least one additional reservoir cap layer beneath the outer reservoir caps and first release system layer.

* * * * *